(12) United States Patent
Leung et al.

(10) Patent No.: US 8,855,759 B2
(45) Date of Patent: Oct. 7, 2014

(54) METHOD OF TREATING A RHEUMATIC DISORDER USING COMBINATION OF TRANSCUTANEOUS ELECTRICAL NERVE STIMULATION AND A GINSENOSIDE

(75) Inventors: Mason Chin Pang Leung, Kowloon (CN); Samuel Chun Lap Lo, Kowloon (CN)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 1023 days.

(21) Appl. No.: 11/907,010

(22) Filed: Oct. 9, 2007

(65) Prior Publication Data

US 2009/0093854 A1    Apr. 9, 2009

(51) Int. Cl.
*A61N 1/00* (2006.01)
*A61N 1/04* (2006.01)
*A61N 1/36* (2006.01)
*A61N 1/32* (2006.01)

(52) U.S. Cl.
CPC .......... *A61N 1/0456* (2013.01); *A61N 1/36021* (2013.01); *A61N 1/36014* (2013.01); *A61N 1/325* (2013.01)

USPC ............................................................ 607/3

(58) Field of Classification Search
CPC ..... A61N 1/36014; A61N 1/34; A61N 1/325; A61N 1/04; A61N 1/05; A61N 1/10–1/18; A61N 1/20; A61N 1/32; A61N 1/0404
See application file for complete search history.

(56) References Cited

U.S. PATENT DOCUMENTS

| | | | |
|---|---|---|---|
| 4,966,893 A | 10/1990 | Pang et al. | |
| 5,137,878 A | 8/1992 | Pang et al. | |
| 2004/0138712 A1* | 7/2004 | Tamarkin et al. | 607/3 |
| 2008/0009469 A1* | 1/2008 | Ninomiya et al. | 514/169 |
| 2008/0027018 A1* | 1/2008 | Mir et al. | 514/44 |
| 2009/0281049 A1* | 11/2009 | Liu et al. | 514/26 |

* cited by examiner

*Primary Examiner* — Carl H Layno
*Assistant Examiner* — Elizabeth K So
(74) *Attorney, Agent, or Firm* — The Hong Kong Polytechnic University

(57) ABSTRACT

The present invention relates to a method of treating rheumatic disorders, and symptoms of arthritis specifically. The method involves utilizing transcutaneous electrical nerve stimulation (TENS) in combination with administration of a ginsenoside, such as Rb1.

5 Claims, 8 Drawing Sheets

METHOD OF TREATING A RHEUMATIC DISORDER USING COMBINATION OF TRANSCUTANEOUS ELECTRICAL NERVE STIMULATION AND A GINSENOSIDE

BACKGROUND

Rheumatic disorder, such as arthritis, generally refer to inflammation, degeneration, or metabolic derangement of the joints and the like. Arthritis is the most common cause of the disorder, affecting 1% of the world's population. Whereas pain is a common complaint, the most devastating effect is inflammation. Non-steroid anti-flammatory drugs (NSAIDs) have been the main form of treatment due to their ability to inhibit production of inflammation-enhancing prostaglandins. However, NSAIDs have been known to be associated with multiple gastrointestinal side-effects, such as gastric ulceration.

Another form of treatment, COX-2 inhibitors, have been found to elevate risk of vascular thrombosis. Another form of treatment, TENS (transcutaneous electrical nerve stimulation), is the procedure of applying controlled, low voltage electrical pulses to the nervous system by passing electricity through the skin via electrodes. TENS is unique in that it exerts pain-relieving effect by activating built-in control mechanisms of the nervous system.

However, following prolonged studies, TENS has been shown not to be a panacea, rather its pain-relieving effect often declined rapidly with time. Thus, it is unknown if TENS provides long term effect.

Ginsenosides are steroid-like compounds found exclusively in the plant genus *Panax*. Ginsenosides, through administration of ginseng, have been known to cause different reactions. Some enhance muscle tone, others regulate blood sugar, and others stimulate the central nervous system. Due to the different effects of ginsenosides, it has difficult to pinpoint which ones may have a beneficial effect on rheumatic disorder. Furthermore, if any benefits were observed they were not substantial.

It is an object of the present invention to provide a new method of treating rheumatic disorders. The new method proposes combining TENS and ginsenosides. Through the new method, inflammation resulting from rheumatic disorders can be addressed synergistically.

DESCRIPTION

The present invention proposes a method of treating rheumatic disorders using a combined regimen of TENS and one or more ginsensosides, such as Rb1.

These and other features, aspects, and advantages of the apparatus and methods of the present invention will become better understood from the following description, appended claims, and accompanying drawings where:

FIG. 1-8 show the effect of combined TENS/Rb1 treatment on concentrations of various cytokines. Combined TENS/Rb1 treatment is compared against TENS treatment and Rb1 treatment. Affected cytokines include IL-10, IL-2, IL-1 alpha, IL-1 beta, Il-6, GM-CSF, IFN-gamma, and TNF-alpha. In many instances, TENS/Rb1 treatment had a synergistic affect on concentration.

The following description of certain exemplary embodiment(s) is merely exemplary in nature and is in no way intended to limit the invention, its application, or uses. Throughout this description, the term "rheumatic disorder" shall refer to a variety of disorders characterized by inflammation, degeneration, or metabaolic derangement of the connective tissue structures of the body, such as the joints; examples include arthritis and osteoarthritis.

The present invention relates to a method of treating a rheumatic disorder in a mammal including the steps of applying a transcutaneous electrical nerve stimulation (TENS)/ginsenoside regimen. The TENS/ginsenoside treatment shows a synergistic effect on increasing cytokine concentration, thus effectively treating rheumatic disorders.

In the present method of treatment, TENS is applied first, followed by administration of the ginsenoside, or vise versa. TENS applies a controlled, low voltage electrical pulse to the nervous system by passing electricity through the skin via electrodes placed on the skin. Units capable of supplying TENS contain one or more of 1 or more electrodes, preferably between 1 to 16 electrodes, a base unit, a connection means such as wires between the electrodes and the, base unit, a stimulus supply means such as a battery source, for example a JV N:Cd rechargeable battery, an intensity varying device such as a knob or lever capable of varying the intensity delivered by the stimulus supply means, and a conductive gel for use as a conduction medium between the electrodes and the patient's skin. In the present invention, the TENS unit is utilized between 20 minutes to 1 hour per session, preferably 20 to 45 minutes. In the present invention, TENS is operated at a frequency between 1 to 50 Hz, preferably between 1 to 4 Hz, more preferably between 1 to 2 Hz. The pulse width can be about 0.15-0.25 ms. In another embodiment, TENS can be delivered in a "pulse-train burst stimulation", which involves delivering impulses at a rate of about 2 Hz with an inner train frequency of about 80 Hz. The intensity of stimulation is increased until phasic muscle contraction occurs. This phasic muscle contraction may be visible.

The electrodes of the TENS Unit can be carbon rubber electrodes, sterile pre-gelled electrodes, a self adhesive electrodes, and may be of a suitable size based upon the body area to be treated. As stated earlier, a conductive gel can be implemented between the electrodes and the patient's skin.

The positioning of the electrodes should be close, i.e., from 0.25 cm to 1 cm, to the affected area or the nearby acupuncture point. The affected area is the area showing symptoms of arthritis, for example swelling, oedma, stiffness, paresthesia, joint pain, etc. For example, the electrodes can be positioned paraspinally at L5-S1 level and sciatic hiatus at midpoint between ischial tuberosity and greater trochanter, paraspinally at cervicothoracic junction, paraspinally at lumbosacral junction, superior to lateral joint line in depression above femoral condyle and medial joint line between tendons of semitendinosus and semimembranosus, 5 cm above medial aspect of patellar base and anterior-inferior to fibular head and 5 cm above lateral aspect of patellar base and just below medial condyle of tibia, dorsal web space and volar suface of wrist, lateral depression at end of elbow crease, and just above medial epieondyle and antecubital fossa.

The administered ginsenoside can be selected from the group consisting Rb1, Rb2, Rb3, Rc, Rd, Rg3, Rh2, and aglycone PD. In one embodiment, the administered ginsenoside is a combination of two or more ginsenosides. In a preferred embodiment, the administered ginsenoside is Rb1.

The ginsenoside is administered with a pharmaceutically-acceptable carrier, such as a liquid carrier for example saline, glucose, distilled water, and the like, or a solid carriers such as a combination of syrups, binders, extracts, coatings, resins, powders, and the like. The ginsenoside can be administered in a concentration of from 75 to 125 µg/ml. The ginsenoside can be administered in a volume of from 250 µl to 350 µl every two to four days for from 10 to 20 days.

EXAMPLE

The following is an example of method of treaty arthritis or the symptoms of arthritis using the regimen of the present invention.
Simultaneous TENS/Rb1 treatment TENS was firstly applied. Acupuncture points chosen were ST-35 and EX-LE-4 because they are common local points for treating knee problems. Surface electrodes were applied near the acupuncture points. A low-frequency constant mode TENS of 2 Hz and pulse width of 200-µs was used. The intensity was increased until a strong, tolerable, stroking sensation, preferably producing visible phasic muscle contraction. Treatment lasted for 20 minutes and the intensity for the TENS was readjusted, if necessary, after 5 minutes to maintain the desired sensation. Treatment was carried out on alternate days for 8 sessions within 2 weeks.

Rb1 is then administered. The ginsenoside Rb1 was administered to arthritic rats. Administration consisted of applying 300 µl of 100 µg/ml Rb1 sub-cutaneously about 0.5 cm from the affected area, which was the one where there was swelling. Administration occurred every third day for the 2 week period.

FIG. 1 shows the synergistic affect of TENS/Rb1 on increasing the concentration of IL-10. As shown, at 24 hours following application of TENS and Rb1, IL-10 concentration is more than merely TENS or Rb1 singly administered. In fact, as singly administered Rb1 is limited to 2500 pg/ml and singly administered TENS is approximately 3200 pg/ml, it was expected that the TENS/Rb1 treatment should be between 2500 pg/ml to 3200 pg/ml; thus TENS/Rb1 results are clearly unexpected.

FIG. 2 shows the synergistic affect of TENS/Rb1 on increasing the concentration of IL-2. As clearly shown, at 24 hours following treatment, TENS/Rb1 treatment resulted in a IL-2 concentration significantly more than TENS or Rb1 administered singly.

As shown in FIG. 3, IL-1 alpha shows an increase in concentration post-TENS/Rb1 treatment as compared to post-TENS or post-Rb1 treatments. Thus, as IL-1 aplha is associated as a target for pain control, the increase in concentration address pain resulting from the arthritic condition.

Figure 1:
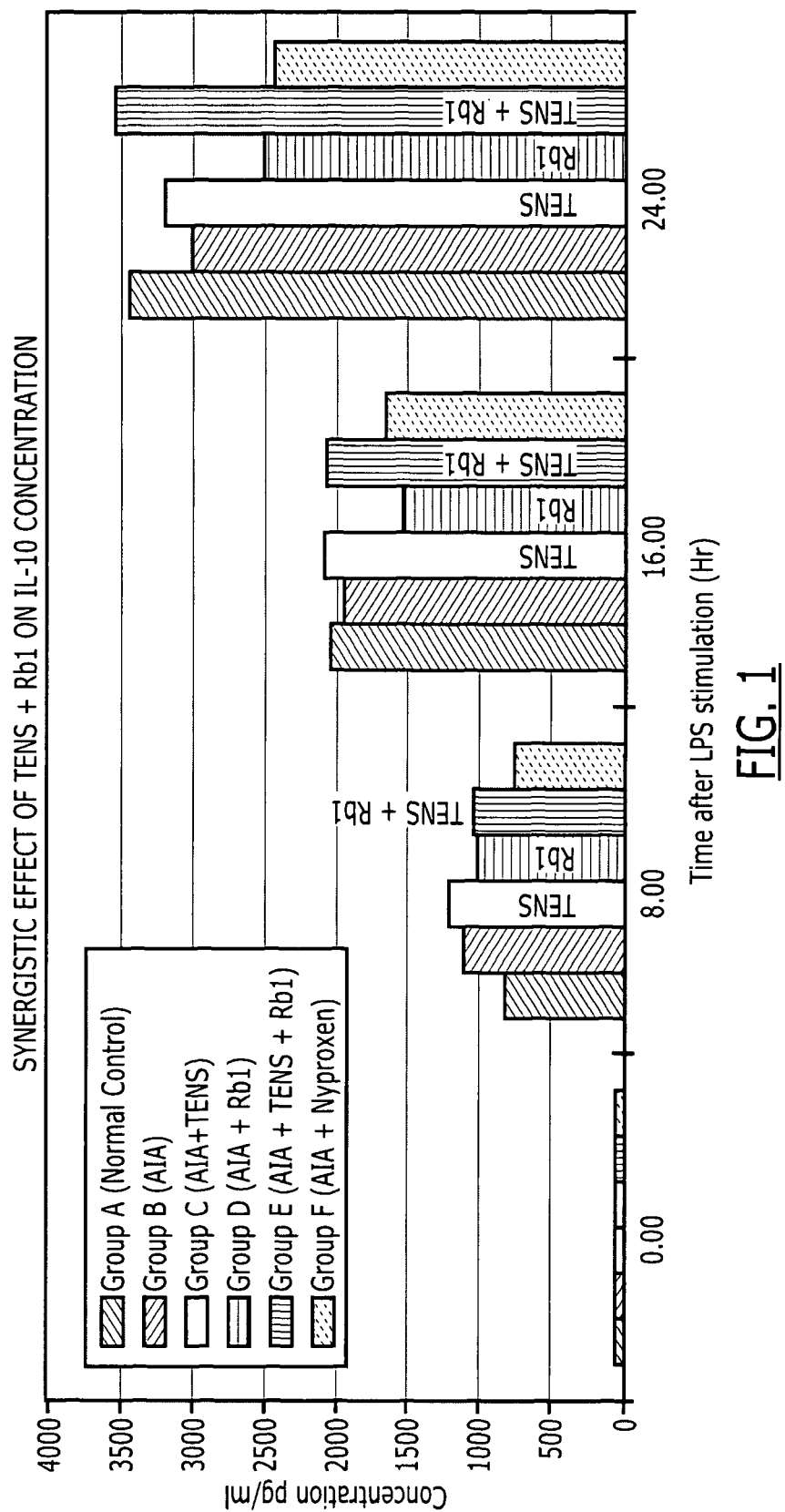
Figure 2:
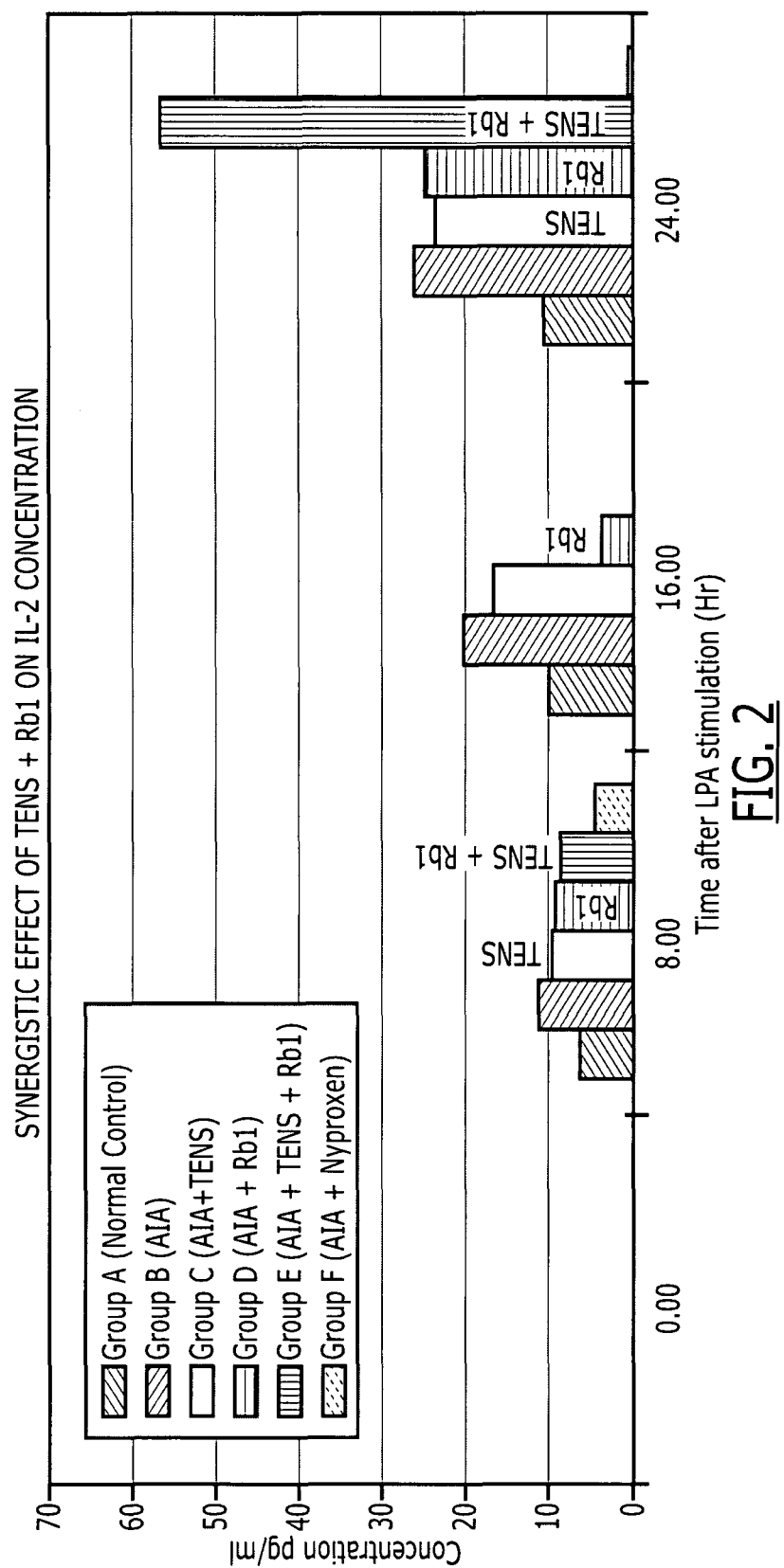
Figure 3:
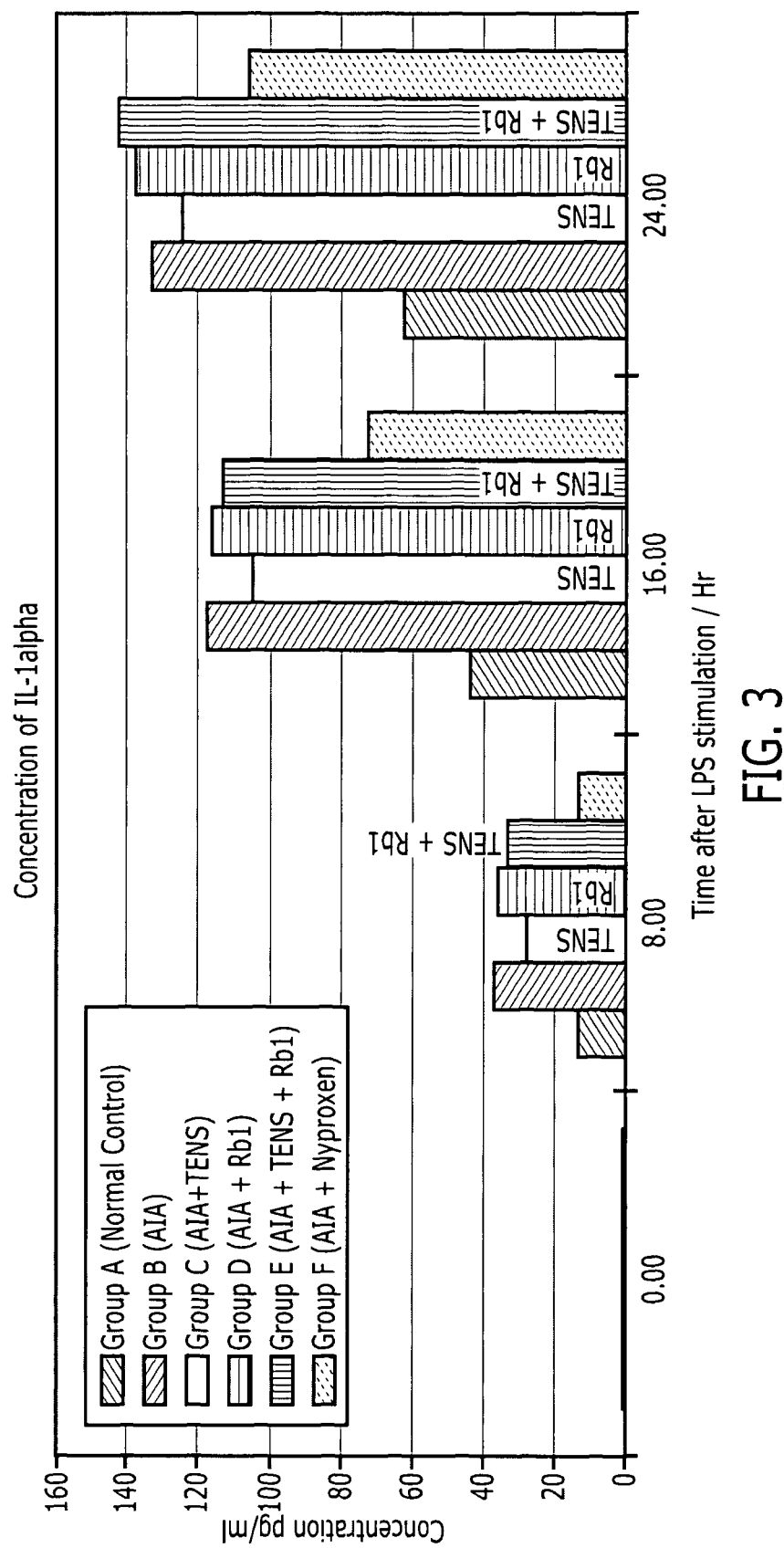
Figure 4:
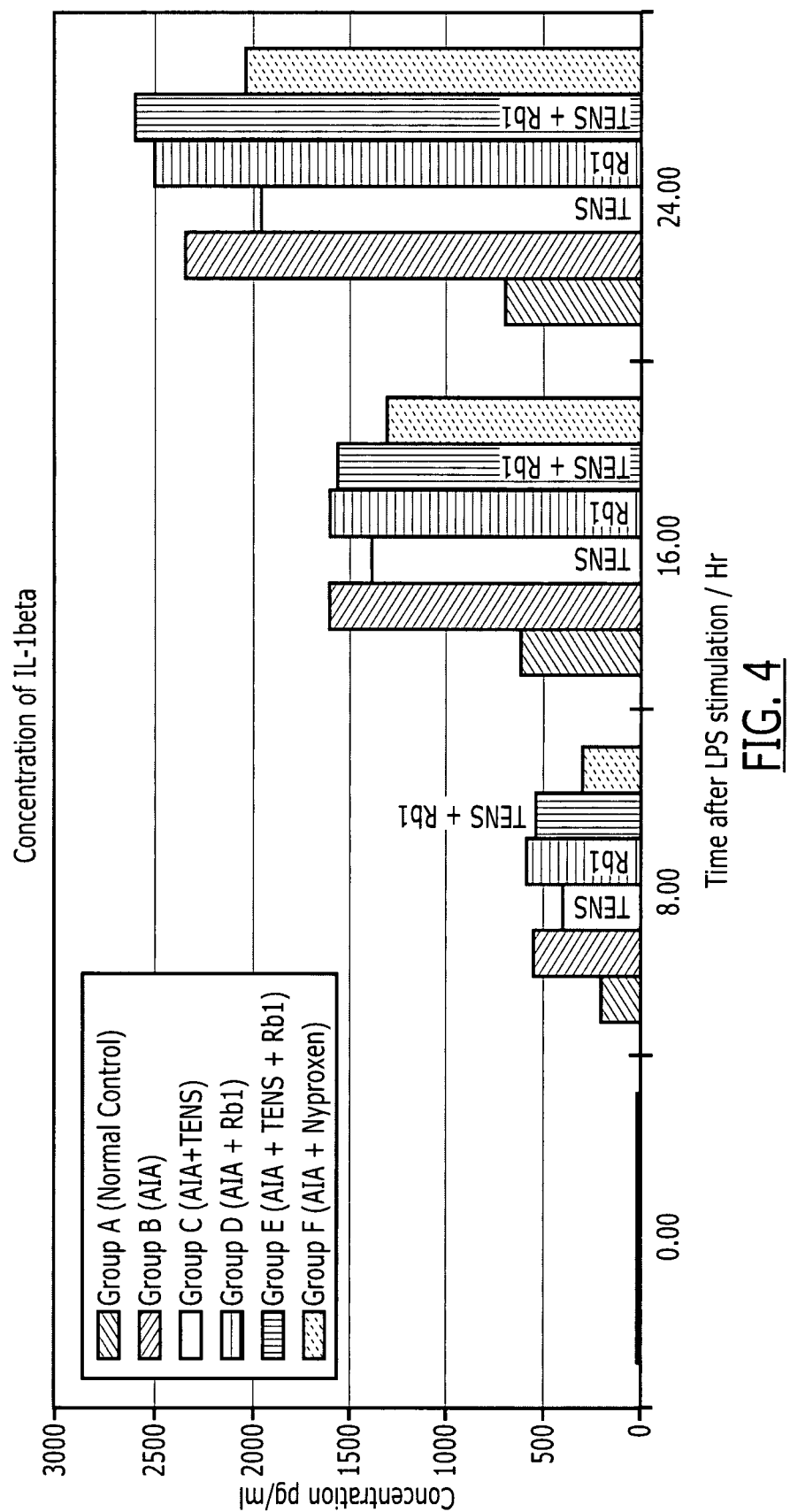
FIG. 4 shows an increase in IL-1 beta concentration post-TENS/Rb1 treatment in comparison to TENS treatment or Rb1 treatment. Similar to IL-1 alpha, IL-1 beta can aid in pain control arising from the arthritic condition.
Figure 5:
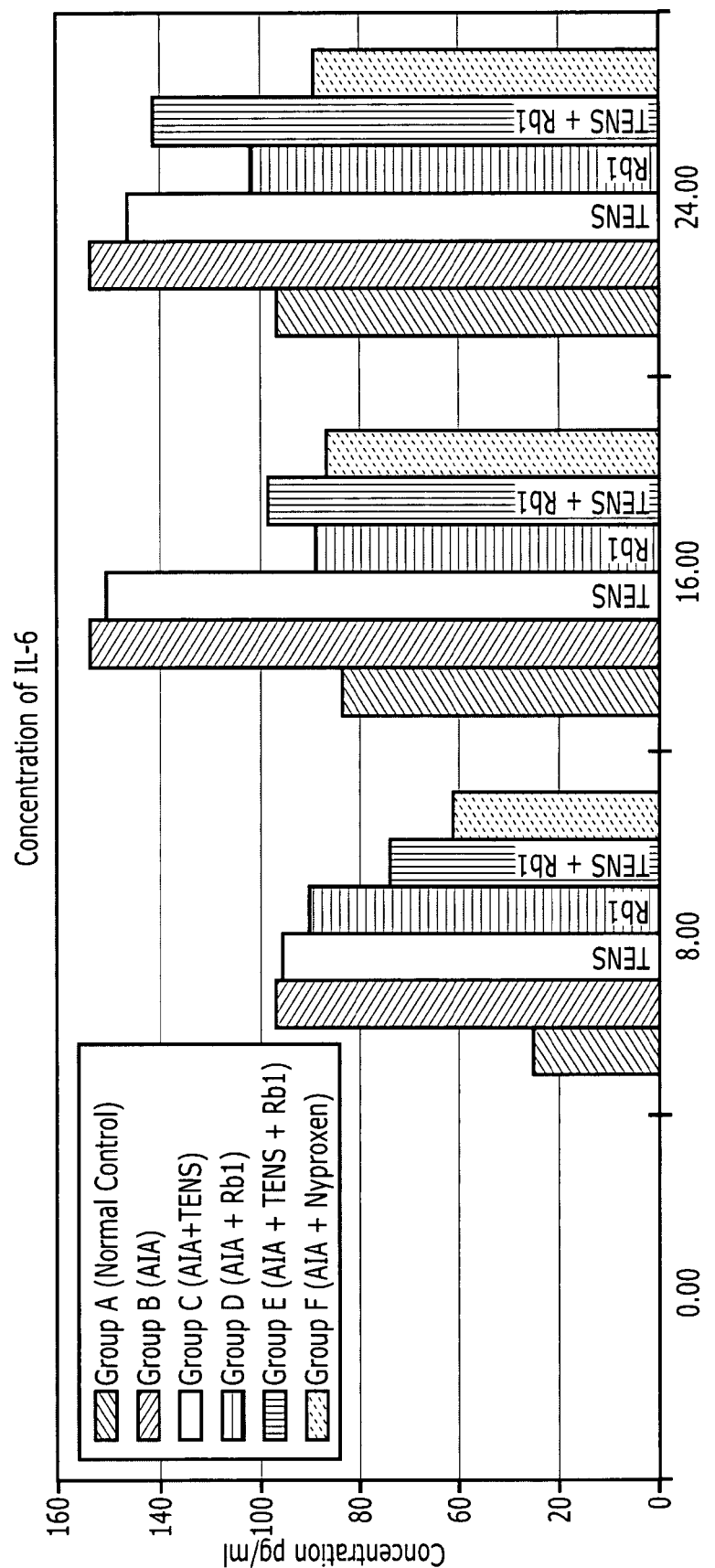
FIG. 5 shows that IL-6 concentration following TENS/Rb1 treatment is lower than concentration following TENS treatment.
Figure 6:
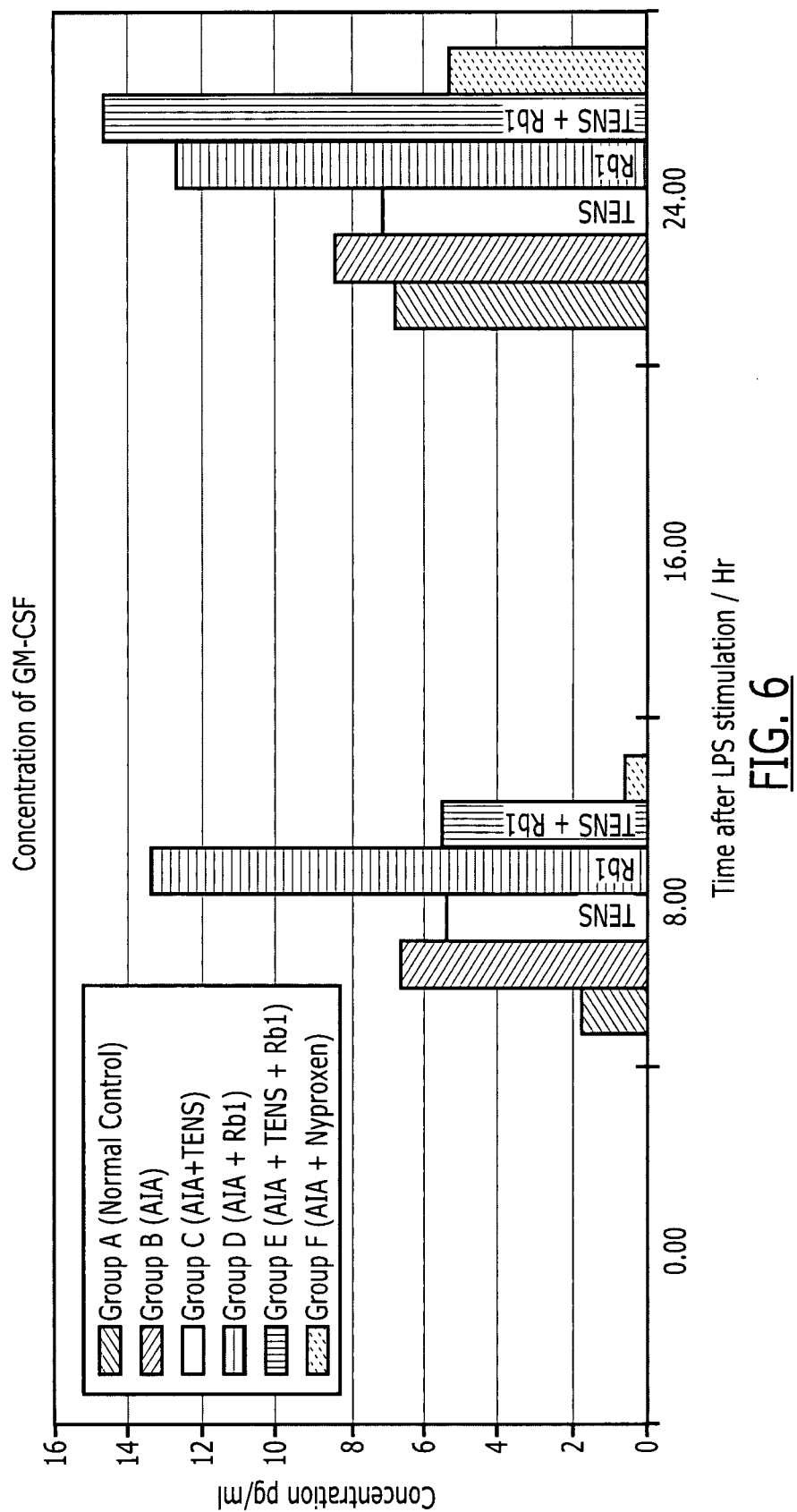

For GM-CSF concentration, see FIG. 6; concentration is higher post-TENS/Rb1 treatments compared with TENS treatment or Rb1 treatment.

Figure 7:
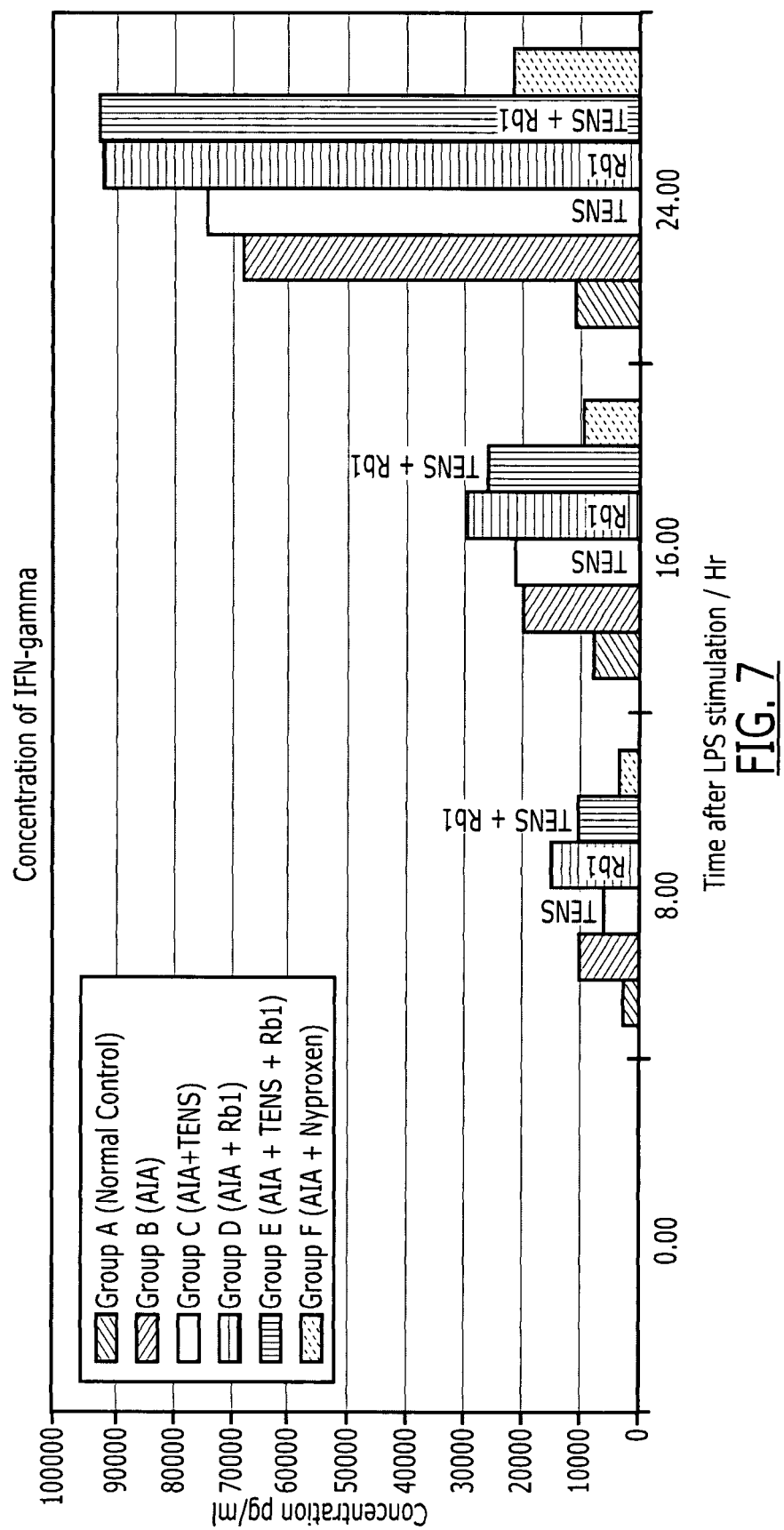
Figure 8:
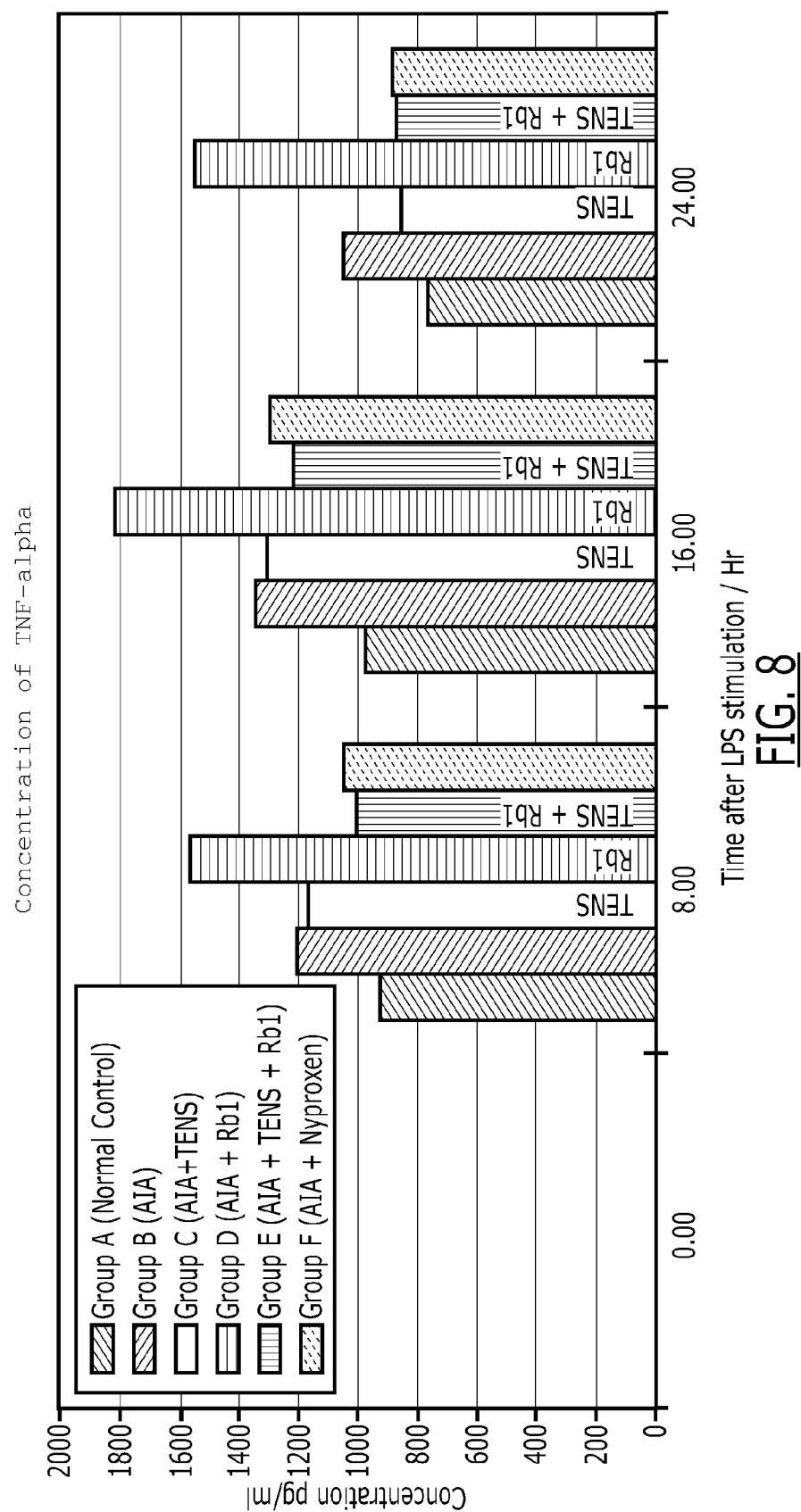

IFN-gamma Post-TENS/Rb1 concentration is almost equal to post-Rb1 concentration (see, FIG. 7).

To TNF-alpha, post-TENS/Rb1 treatment, concentration has decreased, whereas post-Rb1 treatment shows an increase.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A method of treating rheumatic disorders comprising the steps of;
applying transcutaneous electrical nerve stimulation (TENS) 0.25 cm to 1 cm away from an affected area, and followed by
administering a ginsenoside (Rb 1) having a concentration of from 75 to 125 µg/mL subcutaneously in an amount of from 250 µl to 350 µl on the affected area.

2. The method of treating rheumatic disorders in claim 1, wherein TENS is operated between 1 to 4 Hz for a period of 20 minutes to 1 hour per session.

3. The method of treating rheumatic disorders in claim 1, wherein TENS is applied and said ginsenoside is administered for 8 to 10 sessions within a period of 10 to 20 days.

4. The method of treating rheumatic disorders in claim 1, wherein ginsenoside is administered via injection in the skin.

5. A method of treating symptoms of arthritis, comprising the steps of:
applying transcutaneous electrical nerve stimulation (TENS) from 0.25 cm to 1 cm from an affected area, followed by administering a ginsenoside on the affected area (Rb 1) having a concentration of from 75 to 125 µg/ml subcutaneously in amount from 250 µl to 350 µl wherein TENS is applied and said ginsenoside is administered for 8 to 10 sessions within a period of 10 to 20 days.

* * * * *